(12) United States Patent
Mikolajczyk et al.

(10) Patent No.: US 9,347,946 B2
(45) Date of Patent: May 24, 2016

(54) METHODS AND REAGENTS FOR SIGNAL AMPLIFICATION

(75) Inventors: Stephen D. Mikolajczyk, San Diego, CA (US); Lisa S. Millar, San Diego, CA (US)

(73) Assignee: BIOCEPT, INC., San Diego, CA (US)

( * ) Notice: Subject to any disclaimer, the term of this patent is extended or adjusted under 35 U.S.C. 154(b) by 0 days.

(21) Appl. No.: 13/241,083

(22) Filed: Sep. 22, 2011

(65) Prior Publication Data

US 2012/0164661 A1 Jun. 28, 2012

Related U.S. Application Data

(60) Provisional application No. 61/385,937, filed on Sep. 23, 2010.

(51) Int. Cl.
| | |
|---|---|
| *G01N 33/533* | (2006.01) |
| *G01N 33/548* | (2006.01) |
| *G01N 33/58* | (2006.01) |
| *G01N 33/52* | (2006.01) |
| *C08B 37/02* | (2006.01) |
| *C08L 5/02* | (2006.01) |

(52) U.S. Cl.
CPC ............ *G01N 33/58* (2013.01); *C08B 37/0021* (2013.01); *C08L 5/02* (2013.01); *G01N 33/52* (2013.01); *G01N 33/533* (2013.01); *G01N 33/548* (2013.01); *G01N 33/583* (2013.01)

(58) Field of Classification Search
CPC .. G01N 33/548; G01N 33/533; G01N 33/583
USPC .......................................... 436/512, 513, 529
See application file for complete search history.

(56) References Cited

U.S. PATENT DOCUMENTS

| | | | | |
|---|---|---|---|---|
| 4,232,119 | A | * | 11/1980 | Carlsson et al. ............ 530/391.5 |
| 4,256,834 | A | * | 3/1981 | Zuk et al. ...................... 435/7.72 |
| 4,576,912 | A | * | 3/1986 | Yaverbaum et al. ........... 435/7.1 |
| 4,615,986 | A | * | 10/1986 | Yoshida ........................ 436/500 |
| 4,801,504 | A | * | 1/1989 | Burdick et al. ................ 428/403 |
| 5,627,078 | A | * | 5/1997 | Karl et al. ...................... 436/512 |
| 5,650,334 | A | * | 7/1997 | Zuk et al. ...................... 436/529 |
| 5,798,276 | A | * | 8/1998 | Haugland et al. ............. 436/546 |
| 5,846,741 | A | | 12/1998 | Griffiths et al. |
| 5,891,741 | A | * | 4/1999 | Siiman et al. ................. 436/529 |
| 5,994,089 | A | * | 11/1999 | Siiman et al. ................ 435/7.24 |
| 6,387,622 | B1 | * | 5/2002 | Siiman et al. ................ 435/6.16 |
| 6,627,460 | B1 | * | 9/2003 | Lihme et al. .................. 436/529 |

(Continued)

FOREIGN PATENT DOCUMENTS

| | | |
|---|---|---|
| WO | WO 99/40438 | 8/1999 |
| WO | WO 2009/070742 | 6/2009 |

OTHER PUBLICATIONS

International Search Report and Written Opinion for International Application No. PCT/US2011/052837, mailed Apr. 13, 2012, 9 pages.

(Continued)

*Primary Examiner* — Mark Shibuya
*Assistant Examiner* — Gary E Hollinden
(74) *Attorney, Agent, or Firm* — Cooley LLP

(57) ABSTRACT

The present invention provides reagents containing binding moieties conjugated to dextran moieties, methods of making such reagents, and use of such reagents in a variety of molecular and cellular assays.

25 Claims, 8 Drawing Sheets

(56) References Cited

U.S. PATENT DOCUMENTS

| | | | |
|---|---|---|---|
| 6,881,536 B1* | 4/2005 | Shah et al. | 435/5 |
| 8,093,005 B2* | 1/2012 | Jarhede et al. | 435/7.1 |
| 8,415,170 B2* | 4/2013 | Lee et al. | 436/518 |
| 9,040,309 B2* | 5/2015 | Nimri | G01N 33/548 436/529 |
| 2001/0031860 A1* | 10/2001 | Mikolajczyk et al. | 530/402 |
| 2002/0058291 A1* | 5/2002 | Mikolajczyk et al. | 435/7.23 |
| 2005/0019573 A1* | 1/2005 | Kai | 428/403 |
| 2007/0037174 A1 | 2/2007 | Rampal et al. | |
| 2010/0081125 A1 | 4/2010 | Xia et al. | |
| 2010/0151501 A1* | 6/2010 | Mikolajczyk et al. | 435/7.23 |
| 2010/0255479 A1* | 10/2010 | Mikolajczyk et al. | 435/6 |
| 2012/0100538 A1* | 4/2012 | Mikolajczyk et al. | 435/6.11 |

OTHER PUBLICATIONS

Supplementary European Search Report for European Application No. 11827572, mailed Apr. 3, 2014, 4 pages.

Batard, P. et al., "Dextramers: New generation of fluorescent MHC class I/peptide multimers for visualization of antigen-specific CD8+ T cells," Journal of Immunological Methods, 310(1-2):136-148 (2006).

Haugland, R. P., "14.5 Fluorescent and Biotinylated Dextrans," In: Handbook of Fluorescent Probes and Research Products, Molecular Probes, Eugene, OR, Ninth Edition, pp. 581-590 (2002).

* cited by examiner

METHODS AND REAGENTS FOR SIGNAL AMPLIFICATION

RELATED APPLICATIONS

This application claims priority to U.S. Provisional Application No. 61/385,937 filed Sep. 23, 2010, which is hereby incorporated by reference in its entirety.

FIELD OF THE INVENTION

The present invention relates to reagents useful for detection assays, e.g., reagents containing binding moieties conjugated to dextran moieties.

BACKGROUND OF THE INVENTION

During the process of isolating rare cells from blood or other biological samples, it is necessary to identify the target cells from among the other nucleated cells that may be present in a sample. When isolating rare cells, a variety of other cells may also be present, such as for example white blood cells (WBCs). For isolating circulating tumor cells (CTCs), the standard method involves staining for epithelial cells using cytokeratin antibody, and ruling out false positive cytokeratin stained cells by also staining with anti-CD45 antibody, in a effort to detect only CTCs.

In pending US Patent Application No. 20100255479, which is hereby incorporated by reference in its entirety, methods for using multiple antibodies for CTC capture are described.

Despite the availability of these methods, additional detection reagents and methods are needed for detection of cells, such as CTCs. Such reagents and methods would allow for diagnostic assays as well as other clinically relevant assays.

The present invention describes reagents and methods useful for detection of cells in biological samples. For example, the present invention provides reagents and methods that can be used for detection of rare cells, such as CTCs in biological samples.

BRIEF SUMMARY OF THE INVENTION

The present invention is based at least in part on the discovery that a plurality of dextrans and their configuration can be used as part of detectable reagents. Accordingly the present invention provides detectable reagents containing a plurality of dextrans useful for various detection assays, e.g., cell detection assays. In some embodiments, the present invention provides detectable reagents containing a binding moiety conjugated to a dextran component. The dextran component can be additionally attached to a detectable entity.

In some embodiments, the dextran component of the detectable reagent contains about 2 to about 10 dextrans, about 4 to about 8 dextrans or about 6 dextrans. Each dextran can be from about 10 kDa to about 200 kDa molecular weight, about 30 kDa to about 100 kDa molecular weight, or about 50 kDa to about 70 kDa molecular weight. In some embodiments, the dextran is about 70 kDa molecular weight.

In some embodiments, the dextran component comprises more than one dextran, where each dextran has substantially the same molecular weight. In some embodiments, the dextran component comprises more than one dextran, where at least one dextran has a molecular weight different from another dextran.

In some embodiments, the detectable entity is a fluorophore, which can be selected from a fluorophore with green fluorescence, orange fluorescence, red fluorescence, and far red fluorescence. In some embodiments, the fluorophore is selected from a fluorophore with excitation and emission spectra in the range of about 350 nm to about 775 nm. In some embodiments, the fluorophore is selected from a fluorophore with excitation and emission spectra of about 346 nm/446 nm, about 494 nm/519 nm, about 554 nm/570 nm, about 555 nm/572 nm, about 590 nm/617 nm, about 651 nm/672 nm, about 679 nm/702 nm or about 749 nm/775 nm.

In some embodiments, the binding moiety of the detectable reagent is selected from avidin, streptavidin, biotin, digoxigenin, immunoreagent, oligonucleotide, peptide nucleic acid, protein A and protein G.

The present invention provides methods of making a detectable reagent by providing a dextran component, conjugating the dextran component with a binding moiety where the reaction forms a dextran-binding moiety complex; and then attaching a detectable entity to the dextran-binding moiety complex.

The present invention provides methods for making a detectable regent by conjugating a binding moiety to a dextran to form a core dextran-binding moiety, reacting the core dextran-binding moiety with a dextran to form a dextran-binding moiety complex, then attaching a detectable entity to the core dextran-binding moiety complex. In some embodiments, the binding moiety is avidin.

The present invention provides a method for detecting or quantifying a target molecule by contacting the detectable reagent of claim 1 with a sample suspected of containing a target molecule, where the binding moiety is capable of binding to the target molecule, and detecting the signal of the detectable entity attached to the dextran component thereby detecting or quantifying the target molecule.

The present invention provides a reagent comprising a plurality of inter-connected dextrans, where the reagent comprises at least two dextrans. In some embodiments, the total molecular weight is at least 500 kDa. In some embodiments, the plurality of inter-connected dextrans is configured in a layered configuration or branched configuration. In some embodiments, the plurality of inter-connected dextran is attached to a detectable entity.

DETAILED DESCRIPTION

Figure 1:
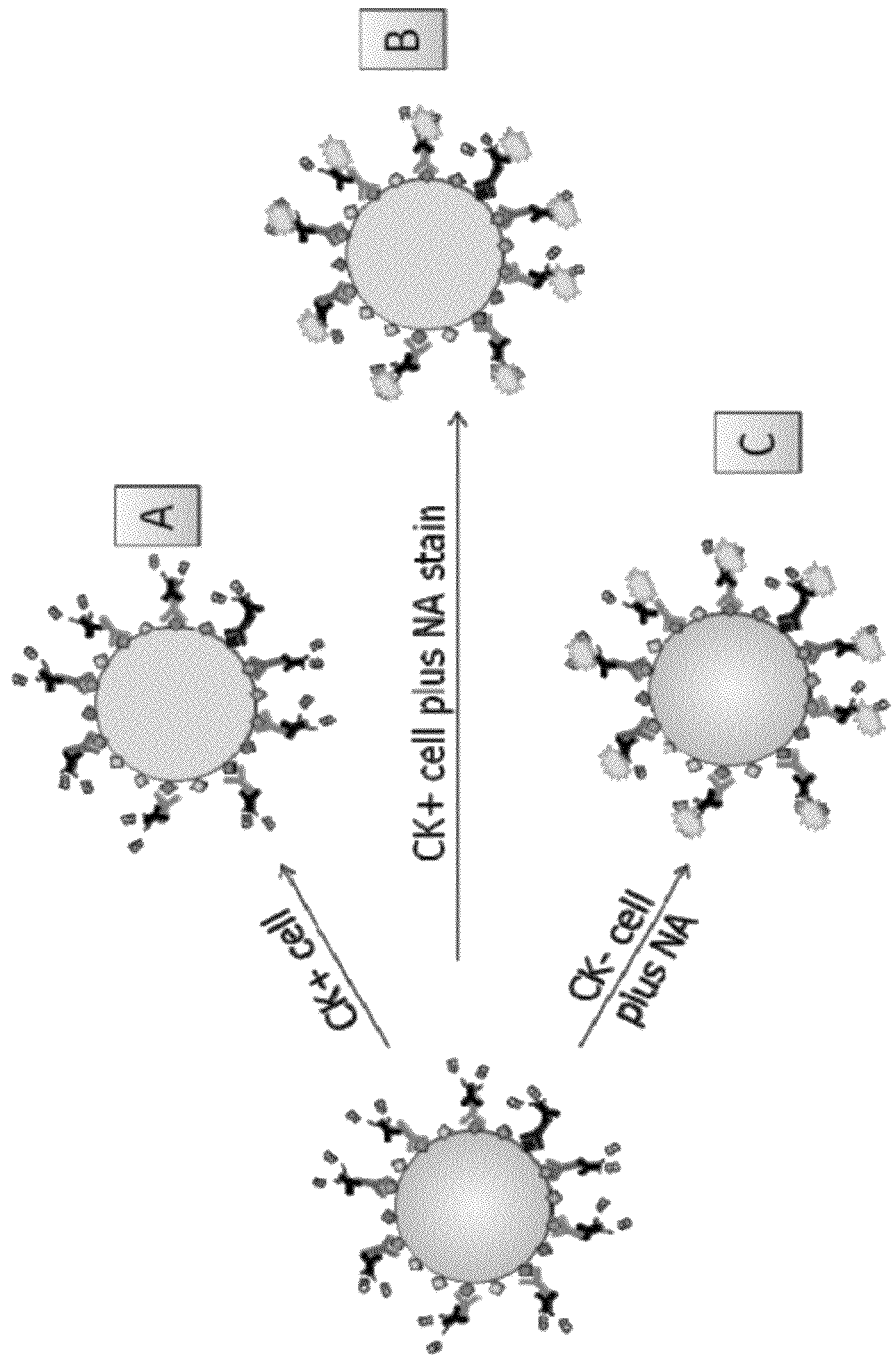
FIG. 1: Enhanced staining—Targeting Cell Surface Antibodies of Captured Cell. Shows three different types of staining methods that can be used to detect cells that have been captured with the antibody cocktail on the micro-channel. In reaction A the captured cells were stained with anti-CK as is commonly employed in the CTC field. Cytokeratin is a cytoplasmic protein and the cell is stained by incubating with anti-cytokeratin antibody labeled with a green fluorescent dye (designated as 488). In reaction B the same cell was further stained by adding avidin labeled with 488 dye (avidin-488). In this case the antibody stained the cytoplasmic CK and the avidin further stained the surface of the cell by binding to the capture antibodies which had been labeled with biotin. Both stains were additive, leading to higher labeling of the cell. An experimental example of this is seen in FIG. 2. In reaction C, the cell was not stained with cytokeratin, but only with the avidin-488. In this case the cell was visualized solely on the basis of the number of avidins binding to the biotinylated capture antibodies on the surface of the cell. An experimental example of this is shown in FIG. 3.

The present invention is based at least in part on the discovery that a plurality of dextrans and their configuration can be used as part of detectable reagents. Accordingly the present invention provides detectable reagents containing a plurality of dextrans useful for various detection assays, e.g., cell detection assays. In some embodiments, the present invention provides detectable reagents containing a binding moiety conjugated to a dextran component. The dextran component can be additionally attached to a detectable entity.

According to the present invention, the dextran component of the detectable reagent can be any combination of a plurality of dextrans, e.g., a combination of at least 2, 3, 4, 5, 6, 7, 8, 9, 10, or more inter-connected dextrans. In some embodiments, the plurality of dextrans are configured or inter-connected in a way to maximize the availability of its sites for attachment of detectable entities. In other embodiments, the plurality of dextrans are configured or inter-connected in a branched configuration. In some other embodiments, the plurality of dextrans are configured or inter-connected in a layered configuration. For example, a plurality of dextrans can be layered on top of each other in an orderly or non-orderly fashion. In some other embodiments, the plurality of dextrans are configured or inter-connected so that each dextran is attached to at least another dextran. In still some other embodiments, the plurality of dextrans are configured or inter-connected so that each dextran is attached to at least 2, 3, 4, 5 or more other dextrans.

In still some other embodiments, the plurality of dextrans are interconnected directly or indirectly. For example, dextrans can be interconnected directly via known methods such as derivatization. In some embodiments, the plurality of dextrans are interconnected indirectly, e.g., via an entity or molecule capable of introducing functional groups or reactive sites. In some other embodiments, the plurality of dextrans are interconnected indirectly via one or more molecules capable of providing functional groups, e.g., thiol or maleimide groups for attachment of other entities including dextrans or detectable entities. In some embodiments, the plurality of dextran are interconnected indirectly via one or more entities, e.g., cross-linking agents, proteins or nucleic acids, which can also provide attachment sites for detectable entities.

In yet some embodiments, the dextran component contains about 2 to about 40 dextrans. In some embodiments, the dextran component contains about 2 to about 30 dextrans. In some embodiments, the dextran component contains about 2 to about 20 dextrans. In some embodiments, the dextran component contains about 2 to about 10 dextrans. In some embodiments, the dextran component contains about 4 to about 8 dextrans. In some embodiments, the dextran component contains about 4, about 6 or about 8 dextrans.

The dextrans of the dextran component of the present invention can have varying molecular weights. In some embodiments each dextran is from about 10 kDa to about 200 kDa molecular weight. In some embodiments each dextran is from about 30 kDa to about 100 kDa molecular weight. In some embodiments, each dextran is from about 50 kDa to about 70 kDa molecular weight. In some embodiments, each dextran is about 70 kDa molecular weight.

The dextran component of the present invention can include dextrans of similar molecular weights or a mixture of dextrans of different molecular weights. In some embodiments, each dextran has substantially the same or the same molecular weight. For example, the dextran component can be a combination of all 10 kDa dextrans, all 30 kDa dextrans, all 70 kDa dextrans, all 100 kDa dextrans or all 200 kDa dextrans. In other embodiments, the dextran component contains a mixture of dextrans where at least one dextran has a molecular weight that is substantially different from another dextran. For example, the dextran component can be any combination of 10 kDa dextrans, 30 kDa dextrans, 70 kDa dextrans, 100 kDa dextrans and 200 kDa dextrans. In yet other embodiments, the dextran component contains a mixture of low molecular weight dextrans and high molecular weight dextrans. In still some other embodiments, the dextran component contains a mixture of dextrans where the total molecular weight of these dextrans adds up to a predetermined molecular weight, e.g., from about 500 kDa to about 1000 kDa, 1500 kDa, 2000 kDa, or more.

The dextran component of the present invention can be made by any suitable methods known or available in the field. For example, the dextran component can be made by sequentially derivatizing desired dextrans using standard derivatization procedures.

The detectable entity can be any detectable entity known to one of skill in the art, including fluorophores, enzymes (such as but not limited to peroxidase or alkaline phosphatase), heavy medals (such as but not limited to gold or ferritin), radioactive labels or any other molecule that is known by one of skill in the art for use in detection of a target entity. Detectable entities can include those used in fluorescence detection assays, enzymatic detection assays, gold detection assays, radioactive labels such as radioactive phosphorous (such as $^{31}P$, $^{32}P$ or $^{33}P$), sulphur (such as $^{32}S$ or $^{35}S$), and digoxigenin.

In some embodiments, the detectable entity is a fluorophore. Fluorophores are commercially available and any known and/or commercially available fluorophore can be employed as the detectable entity for the present invention. In some embodiments, the fluorophore exhibits green fluorescence (such as for example 494 nm/519 nm), orange fluorescence (such as for example 554 nm/570 nm), red fluorescence (such as for example 590 nm/617 nm), or far red fluorescence (such as for example 651 nm/672 nm) excitation/emission spectra. In some embodiments, the fluorophore is a fluorophore with excitation and emission spectra in the range of about 350 nm to about 775 nm. In some embodiments the excitation and emission spectra are about 346 nm/446 nm, about 494 nm/519 nm, about 554 nm/570 nm, about 555 nm/572 nm, about 590 nm/617 nm, about 651 nm/672 nm, about 679 nm/702 nm or about 749 nm/775 nm.

In some embodiments, the fluorophore can include AlexaFluor 3, AlexaFluor 5, AlexaFluor 350, AlexaFluor 405, AlexaFluor 430, AlexaFluor 488, AlexaFluor 500, AlexaFluor 514, AlexaFluor 532, AlexaFluor 546, AlexaFluor 555, AlexaFluor 568, AlexaFluor 594, AlexaFluor 610, AlexaFluor 633, AlexaFluor 647, AlexaFluor 660, AlexaFluor 680, AlexaFluor 700, and AlexaFluor 750 (Molecular Probes AlexaFluor dyes, available from Life Technologies, Inc. (USA)). In some embodiments, the fluorophore can include but is not limited to Cy dyes, including Cy2, Cy3, Cy3B, Cy3.5, Cy5, Cy5.5 and Cy7 (available from Lumiprobes). In some embodiments the fluorophore can include but is not limited to DyLight 350, DyLight 405, DyLight 488, DyLight 550, DyLight 594, DyLight 633, DyLight 650, DyLight 680, DyLight 750 and DyLight 800 (available from ThermoScientific (USA)). In some embodiments, the fluorophore can include but is not limited to a FluoProbes 390, FluoProbes 488, FluoProbes 532, FluoProbes 547H, FluoProbes 594, FluoProbes 647H, FluoProbes 682, FluoProbes 752 and FluoProbes 782.

The binding moiety can include any molecule or groups of molecules that are capable of binding to another molecule or group of molecules, including but not limited to protein and nucleic acid based binding moieties. A variety of binding moieties are known in the art and any known binding moiety can be contemplated for use with the methods of the present invention. In some embodiments, the binding moiety includes but is not limited to avidin, streptavidin, biotin, digoxigenin, an immunoreagent, an oligonucleotide or derivative thereof, a peptide or derivative thereof, a nucleic acid or derivative thereof, a peptide nucleic acid or derivative thereof, and protein A and protein G ligand-binding portions thereof. An immunoreagent can include but is not limited to an antibody or antigen-binding portion thereof, and can include for example a Fab fragment.

According to another aspect of the present invention, it provides methods of making a detectable reagent. In some embodiments, these methods include providing a plurality of inter-connected dextrans and conjugating the inter-connected dextrans with a binding moiety. In some other embodiments, these methods optionally include attaching a detectable entity to the inter-connected dextrans.

Methods for making a plurality of inter-connected dextrans are well known in the art. For example, standard NHS (N-hydroxy succinimidyl ester) and iminothiolane amine derivatizing reagents can be used according to standard procedures well known in the field. Conjugating a plurality of inter-connected dextran to a binding moiety can be carried out according to any suitable conjugation methods known or available in the field. In some embodiments, conjugation includes one or more covalent or non-covalent bonds or a combination thereof between two entities, e.g., a plurality of inter-connected dextrans and a binding moiety. In some embodiments, a binding moiety, for example avidin, can be derivatized with iminothiolane. Iminothiolane reactions have been well described in the art (see, for example, ThermoScientific instructions available with commercially purchased iminothiolane; as well as Traut, R. R., et al. *Biochem* 12(17): 3266-3273 (1973)). In some embodiments, derivatization reactions can be performed to achieve a substitution rate of 3-5 thiols per avidin.

In some embodiments, dextran can also be derivatized to form dextran-amine with a commonly used heterobifunctional reagent, SMCC (Succinimidyl-4-[N-maleimidomethyl]cyclohexane-1-carboxylate; Pierce Chemical company, Rockford, Ill.). SMCC reactions have been well described and are well known in the art (see, for example, ThermoScientific instructions available with commercially purchase SMCC; as well as Ishikawa, E., et al., *J Immunoassay* 4:209-327 (1983); Brinkley, M. A., *Bioconjugate Chem* 3:2-13 (1992); and Mattson, G., et al., *Molecular Biology Reports* 17:167-83 (1993)). In some embodiments, the derivatization reaction can be performed to obtain 1-2 maleimide groups per dextran. In some embodiments, a plurality of inter-connected dextrans can be made by sequentially derivatizing a desired amount of dextran.

Detectable entities can be added or attached to the detectable reagent by a variety of methods, all of which are well known in the art. For example, NHS reactions can be employed to add or connect fluorophores (also commonly referred to as fluorescent dyes) to dextran molecules. In some embodiments, the fluorophore can be an NHS ester, a succinimidyl ester (SE) or a tetrafluorophenyl (TFP) ester. Commercially available fluorophores contain detailed instructions for adding the fluorophore to other molecules, and these methods of fluorophore labeling are well known in the art (see for example, product literature available with purchased fluorophores or other detectable entities; as well as Proudnikov D., et al., *Nucleic Acids Research*, 24 (22): 4535-4542 (1996), *Current Protocols in Nucleic Acid Chemistry*, 2003; *Current Protocols in Molecular Biology* (2002); and *Current Protocols in Immunology* (2002).)

In some embodiments methods for making a detectable agent include conjugating a binding moiety with a dextran to form a core dextran-binding moiety and conjugating the core dextran-binding moiety with one or more dextrans, e.g., sequentially adding one or more layers or branches of dextrans to the core dextran-binding moiety. The resulting dextran-binding moiety complex can then be optionally attached to a detectable entity.

In some embodiments dextran can be used to provide primary reactive sites, e.g., when using amine reactive derivatives of NHS esters. In some other embodiments, dextran can be used to introduce secondary functionalities, functional groups or reactive sites, e.g., thiol or maleimide groups useful for reacting with or connecting to other molecules such as dextrans or detectable entities. In some other embodiments, dextran can be used to react with other entities to provide further functional groups, reactive sites or binding sites, e.g., for connecting with dextrans or detectable entities. For example, proteins such as phycoethrythrin can be attached to the dextran to provide endogenous levels of fluorescence labeling instead of using NHS esters of fluorescent molecules. In another example, nucleic acids can be introduced into the dextran to serve as secondary binding sites for other molecules in a reaction or they can serve as probes for additional functionality.

In yet other embodiments, the present invention provides methods for making an avidin-based detectable agent. In some embodiments, the methods can include derivatizing a dextran-amine to generate maleimide groups and derivatizing an avidin to generate thiol groups. Then reacting the derivatized avidin with a molar ratio of one or more derivatized dextran-amine molecules where reacting derivatized avidin with derivatized dextran-amine results in a dextran-avidin. Then derivatizing the dextran-avidin to generate one or more thiol groups per dextran and further reacting the derivatized dextran-avidin with a molar ratio of one or more maleimide-derivatized dextran amine molecules where the reaction between the derivatized dextran-avidin and the maleimide-derivatized dextran amine results in a layered or branched dextran-avidin complex. Then optionally reacting the dextran-avidin complex with a molar ratio of one or more detectable entities, where the reaction of the dextran-avidin complex with the detectable entity results in a detectable reagent of the present invention.

In some embodiments, the avidin was derivatized with iminothiolane to obtain 3-5 thiols per avidin. A 3-fold molar excess of 70 kDa dextran-amine which had been derivatized with 1-2 maleimide groups using a commonly used heterobifunctional reagent, SMCC (Succinimidyl-4-[N-maleimidomethyl]cyclohexane-1-carboxylate, Pierce Chemical company, Rockford, Ill.) was then added. The avidin-dextran was further derivatized with iminothiolane to achieve a substitution rate of 2-3 thiols per dextran, and then further incubated with a 6-fold molar excess of dextran over the original avidin. The dextran-avidin complex can then be labeled with a 10-fold excess of NHS-fluorophore over dextran. In some embodiments, the fluorophore is AlexaFluor 488 or AlexaFluor 546.

The molar ratios of reagents can be adjusted to obtain the desired number of maleimide groups, thiol groups or the desired degree of labeling with the detectable entity, and such modifications are well known in the art. Reactions can be readily adjusted by one of skill to achieve the reactions desired. For example, reactions can be modified to obtain specific numbers of maleimide and thiol groups as desired for particular applications.

The present invention also provides methods for detecting or quantifying a target molecule. Such methods include contacting the detectable agent of the present invention with a sample suspected of containing a target entity where the binding moiety of the detectable reagent is capable of binding to the target entity and then detecting the detectable entity signal in order to detect or quantify the target molecule. A target entity can include but is not limited to a protein, group of proteins, a peptide, a nucleic acid or a cell.

A sample can include any biological or non-biological sample. In some embodiments, a sample includes any unprocessed or processed cell, tissue and/or human secretion samples. In some other embodiments, a sample includes any nucleic acid, protein, or sub-cellular components isolated or purified, partially or wholly, from a raw biological sample. In yet some other embodiments, a sample useful for the present invention includes but is not limited to serum, blood, plasma, whole blood and derivatives thereof, skin, hair, hair follicles, saliva, oral mucous, vaginal mucous, sweat, tears, epithelial tissues, urine, semen, seminal fluid, seminal plasma, prostatic fluid, pre-ejaculatory fluid (Cowper's fluid), excreta, biopsy, ascites, cerebrospinal fluid, lymph, and tissue extract sample or biopsy or a combination thereof. (See, e.g., *Clinical Proteomics: Methods and Protocols*, Vol. 428 in *Methods in Molecular Biology*, Ed. Antonia Vlahou (2008); and Holland, N., *Mutation Research/Reviews in Mutation Research*, 543 (3): 217-234 (2003); all of which are incorporated herein by reference in their entireties.)

For methods related to detection and quantitation, such methods are well known in the art and any standard methods can be employed. One of skill will readily understand which methods to employ based on the detectable entity to be employed with the detectable reagent of the present invention. Such detection and quantitation protocols are well known and any standard methods can be employed. (See, for example, *Current Protocols in Molecular Biology*, Ed. Ausubel, Frederick M. (2010); *Current Protocols in Protein*

Science Last, Ed. Coligan, John E., et al. (2010); *Current Protocols in Nucleic Acid Chemistry*, Ed. Egli, Martin (2010); and *Molecular Cloning: A Laboratory Manual*, Third Edition, Sambrook, Joseph (2001), all of which are incorporated herein by reference in their entireties.)

The detectable reagent of the present invention can find use with immunoassays (such as ELISA), cell sorting assays (such as but not limited to FACS), flow cytometry assays, nucleic acid assays, protein assays, drug interaction assays, microfluidic assays, rare cell detection or quantitation, or any other of a variety of sorting, detection or quantitation assays that are presently used and described in the art. Such assays can be manual or automated. In some embodiments, the reagents of the present invention find use with for example micro-channels or other microfluidic devices.

The detectable reagent of the present invention can be used for detection and quantitation of target entities (such as molecules, proteins and/or nucleic acids). Such target entities can also include rare cells. In some embodiments, rare cells can include any cells that are not normally present in a biological sample and may be present as an indicator of a disease or abnormal condition. In some embodiments, these cells are present at about one or more order of magnitude less than other cells in the sample. Such diseases or conditions can include chronic disease (such as cancer), injury or pregnancy. In some embodiments, rare cells can include cells normally present in biological specimens, but that are present with a frequency that is about one or more orders of magnitude less than other cells present in a sample. Rare cells can include but are not limited to circulating tumor cells (CTCs), fetal cells and stem cells.

Methods for comparing signals from various detectable entities are well known in the art and one of skill would readily know how to perform such comparison analyses. Enhanced, increased and/or amplified detection can be in comparison to a binding moiety directly conjugated to one or more detectable entities or a binding moiety conjugated to a single dextran containing one or more detectable entities. Enhanced, increased and/or amplified detection can include for example reduced binding to non-target entities (such as for example, reduced binding to white blood cells, WBCs), reduced non-specific binding, increased detectable entity signal (such as for example, increased light signal from the fluorophores, increased radioactive signal from radiolabels, or increased light from enzymatic reactions), as well as increased assay sensitivity (for example, the level of detection of rare cells in a sample can be increased so that more rare cells are detected). Increased selectivity in detection of the target entity, such as CTCs, fetal cells, stem cells or other rare cells can also be achieved using the detectable agent of the present invention. The detectable agent of the present invention can be used to enhance the detection of CK stained cells in clinical samples, as well as be used to detect cells that contain no CK stain in a variety of assays, in order to increase the number of CTCs detected in a sample.

In some embodiments, the detectable reagents of the present invention provide enhanced, increased and/or amplified detection when compared to the detection achieved from a binding moiety conjugated to detectable entities in the absence of the dextran component of the invention or a binding moiety conjugated to a single dextran containing one or more detectable entities. In some embodiments, when the detectable reagent of the present invention is conjugated to a detectable entity, the detectable reagent gives 2, 3, 4, 5, 6, 7, 8, 9, 10, or more fold more signal. In some embodiments, the detectable reagent of the present invention has reduced or decreased non-specific binding to non-target entities. In some embodiments, the reduced non-specific binding results in a detectable agent with a 5, 6, 7, 8, 9, 10 or more increased/better signal to noise ratio.

EXAMPLES

The following examples are offered to illustrate, but not to limit the claimed invention.

Example 1

Enhanced Staining of Cells in the Biocept Micro-Channel Using Fluorescently Labeled Avidin-Dextran Bioconjugates This example describes a reagent and methods for alternate staining that can be used to enhance the detection of CK stained cells in clinical samples, and that can be used to detect cells that contain no CK stain. Enhanced or amplified staining was achieved by conjugating a binding moiety, such as avidin, to an amino-dextran containing a fluorescent label (fluorophore detectable entity). This enhanced version of avidin was several fold brighter than fluorescently labeled avidin, and importantly had lower non-specific binding to non-target cells in the blood. Cumulatively that meant that the fluorescently labeled avidin-dextran was a 5-10 fold superior signal-to-noise ratio. By having less non-specific binding to non-target white blood cells (WBC) this offered a distinct advantage in the selective detection of the captured CTCs.

Preparation of Fluorescently Labeled Avidin-Dextran

Standard NHS and iminothiolane amine derivatizing reagents were used in these experiments. The fundamental reaction conditions for these reagents are well known in the art. However the sequence and molar ratio of incubation for each of these conjugates was important to the ultimate performance of the avidin-dextran conjugate. The following is a preferred embodiment for the preparation of the avidin-dextran conjugate. The avidin was derivatized with iminothiolane to achieve a substitution rate of 3-5 thiols per avidin. To this was added a 3 fold molar excess of 70 kDa dextran-amine which had been derivatized with 1-2 maleimide groups using a commonly used heterobifunctional reagent, SMCC (Succinimidyl-4-[N-maleimidomethyl]cyclohexane-1-carboxylate; Pierce Chemical company, Rockford, Ill.). NHS is N-hydroxy succinimidyl ester. Once complete the avidin-dextran conjugate was further derivatized with iminothiolane to achieve a substitution rate of 2-3 thiols per dextran, and then further incubated with a 6-fold molar excess of dextran over the original avidin. Finally this conjugate was labeled with a 10-fold excess of NHS-fluorescent dye over dextran, either 488 or 546 in the current examples. The molar ratios of maleimide, thiol groups or degree of fluorescent label may be adjusted to achieve modify properties for the conjugate. It was estimated that this process resulted in an avidin with 4-8 dextrans of 70 kDa attached, referred to in this example as avidin-based detectable reagent 70 kDa dextran.

An alternate avidin-dextran conjugate was prepared using a 500 kDa dextran-amine. In this case the same derivatizing reagents were employed. The thiolated avidin was prepared as described above. The 500 kDa dextran-amine was also derivatized with SMCC as described and conjugated to avidin. In this example the 500 kDa avidin-dextran conjugate was then fluorescently labeled with NHS-AlexaFluor 488 at the same molar ratio excess (10-fold) as used in the sequential process using 70 kDa dextran-amine. This agent is referred to in this example as avidin-based reagent 500 kDa dextran.

Results & Discussion

Figure 2:
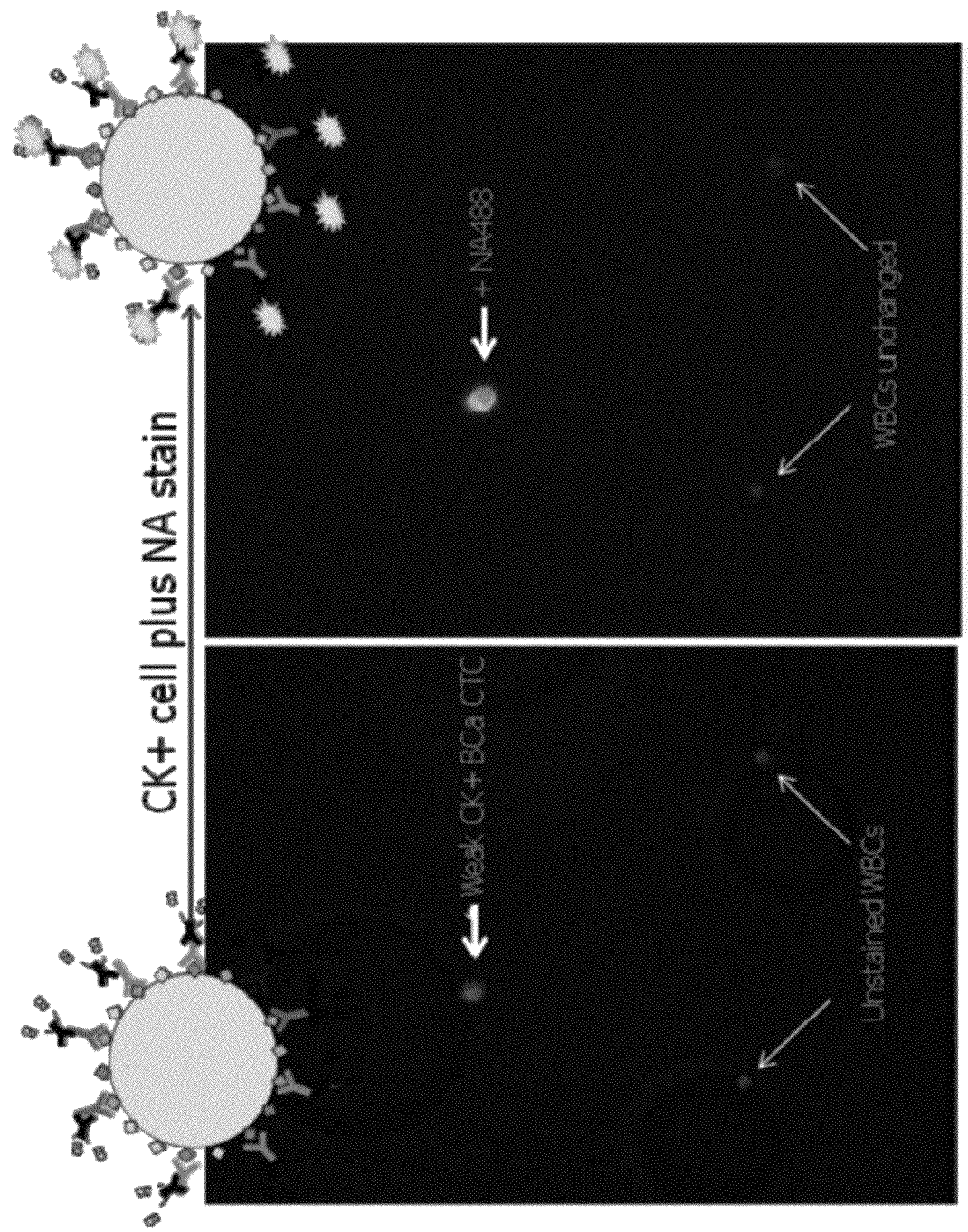
FIG. 2: Detection of cinical CK+ CTCs is enhanced when capture antibodies are used to augment stain. Shows the capture of a breast cancer tumor cell with antibody cocktail, and its detection with CK stain (Panel A). In this case the stain was quite weak, although high enough above background to be identified as a tumor cell. As always, these CTC cells were simultaneously stained with red fluorescently labeled CD45 and this cell is CD45 negative. The location of this cell was recorded and the micro-channel then stained with the avidin-488. Panel B shows the relocation of this cell after avidin-488 treatment and shows that it was much more brightly stained. In both panels white blood cells were observed (nuclear stained with DAPI), but these cells had no detectable stain.

Three different types of staining methods can be used to detect cells that have been captured with the antibody cocktail on the micro-channel (See, FIG. 1). In reaction A, the captured cells were stained with anti-CK as is commonly employed in the CTC field. Cytokeratin is a cytoplasmic protein and the cell is stained by incubating with anti-cytokeratin antibody labeled with a green fluorescent dye (designated as 488). In reaction B, the same cell was further stained by adding the avidin-488 (avidin labeled with 488 dye). In this case the antibody stained the cytoplasmic CK and the avidin further stained the surface of the cell by binding to the capture antibodies which had been labeled with biotin. Both stains were additive, leading to higher labeling of the cell. An example of this is seen in FIG. 2. In reaction C, the cell was not stained with cytokeratin, but only with the avidin-488. In this case the cell was visualized solely on the basis of the number of avidins binding to the biotinylated capture antibodies on the surface of the cell. An experimental example of this is shown in FIG. 3.

The capture of a breast cancer tumor cell with antibody cocktail, and its detection with CK stain (Panel A) is shown in FIG. 2. In this case the stain was quite weak, although high enough above background to be identified as a tumor cell. As always, these CTC cells were simultaneously stained with red fluorescently labeled CD45 and this cell is CD45 negative. The location of this cell was recorded and the micro-channel then stained with the avidin-488. Panel B shows the relocation of this cell after avidin-488 treatment and shows that it was much more brightly stained. In both panels white blood cells were observed (nuclear stained with DAPI), but these cells had no detectable stain.

Figure 3:
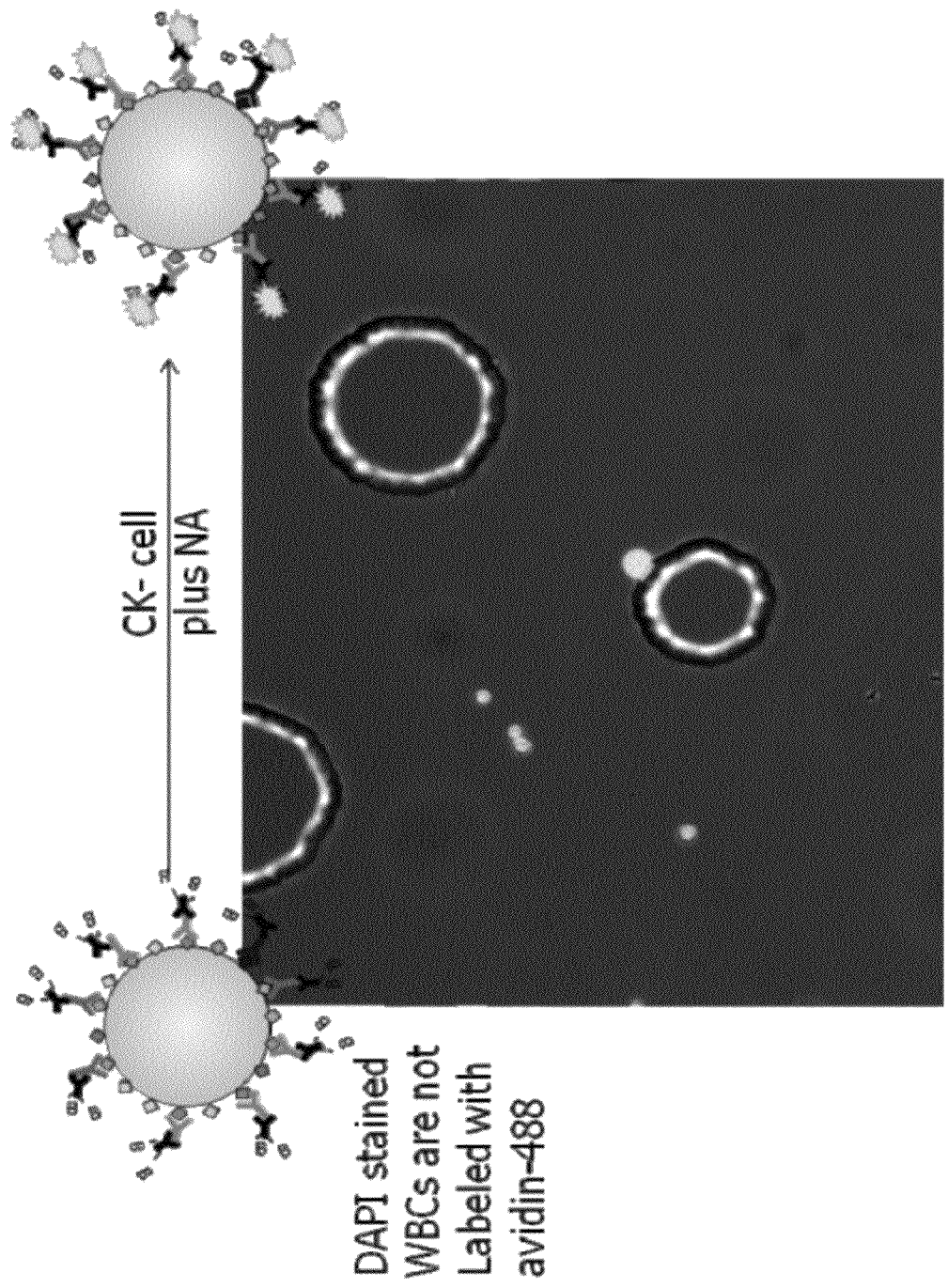
FIG. 3: Detection of Spiked Cells Captured from Blood Based Only on Labeling of Cell Capture Antibodies. Shows an example of cell detection based solely on the staining of the capture antibodies. In this experiment SKOV cells were spiked into blood and the sample processed as usual for the capture of CTCs. While not an absolute measure, the nuclear size of SKOV cells was typically 2-3 times larger than the nucleus of a typical WBC. After staining with avidin-488 only, the SKOV cells were brightly stained while the WBCs had no detectable stain. This demonstrated that cells not stained with CK or cells not containing CK could be detected through labeling of their surface capture antibodies. As described in US Patent Application No. 20100255479, staining could be significantly enhanced by the use of multiple antibodies.

An example of cell detection based solely on the staining of the capture antibodies is shown in FIG. 3. In this experiment SKOV cells were spiked into blood and the sample processed for the capture of CTCs (see, for example, US Patent Application No. 20100255479). While not an absolute measure, the nuclear size of SKOV cells was typically 2-3 times larger than the nucleus of a typical WBC. After staining with avidin-488 only, the SKOV cells were brightly stained while the WBCs had no detectable stain. This demonstrates that cells not stained with CK or cells not containing CK could be detected through labeling of their surface capture antibodies. As described in pending US Patent Application No. 20100255479, this staining could be significantly enhanced by the use of multiple antibodies.

Figure 4:
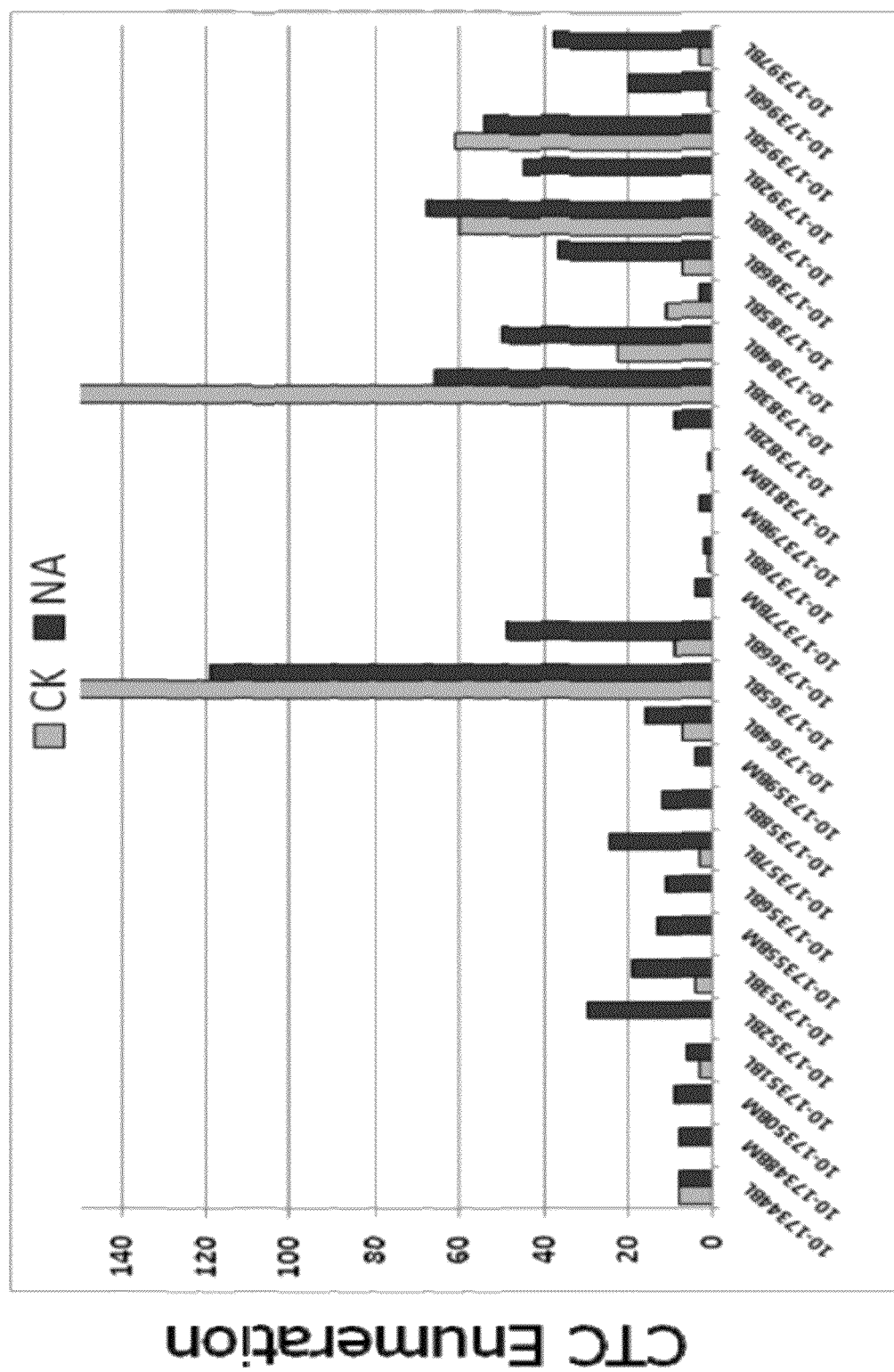
FIG. 4: Enumeration of captured breast cancer cells detected with labeled anti-cytokeratin and labeled Neutravidin. Shows the enumeration of breast cancer samples on the micro-channel. In this experiment the cells were first stained with fluorescently labeled 488 anti-CK antibody under standard conditions. Green labeled cells were detected and their X-Y coordinates on the micro-channel recorded. Next the channels were treated with green fluorescently labeled avidin to label the antibodies on the surface of the cells. The channels were recorded for green fluorescent cells in locations other than recorded for the CK stain. All cells thus identified were also determined to be CD45 negative. The bar chart shows that in most cases the avidin detected significantly more cells than the CK stain. In control experiments using healthy donor blood there were no detectable cells when run under the same conditions and simultaneously stained with anti-CK-488 combined with avidin-488 (data not shown).

The enumeration of breast cancer samples on the micro-channel is shown in FIG. 4. In this experiment the cells were first stained with fluorescently labeled 488 anti-CK antibody under standard conditions. Green labeled cells were detected and their X-Y coordinates on the micro-channel recorded. Next the channels were treated with green fluorescently labeled avidin to label the antibodies on the surface of the cells. The channels were recorded for green fluorescent cells in locations other than recorded for the CK stain. All cells thus identified were also determined to be CD45 negative. The bar chart shows that in most cases the avidin detected significantly more cells than the CK stain. In control experiments using healthy donor blood there were no detectable cells when run under the same conditions and simultaneously stained with anti-CK-488 combined with avidin-488 (data not shown).

Figure 5:
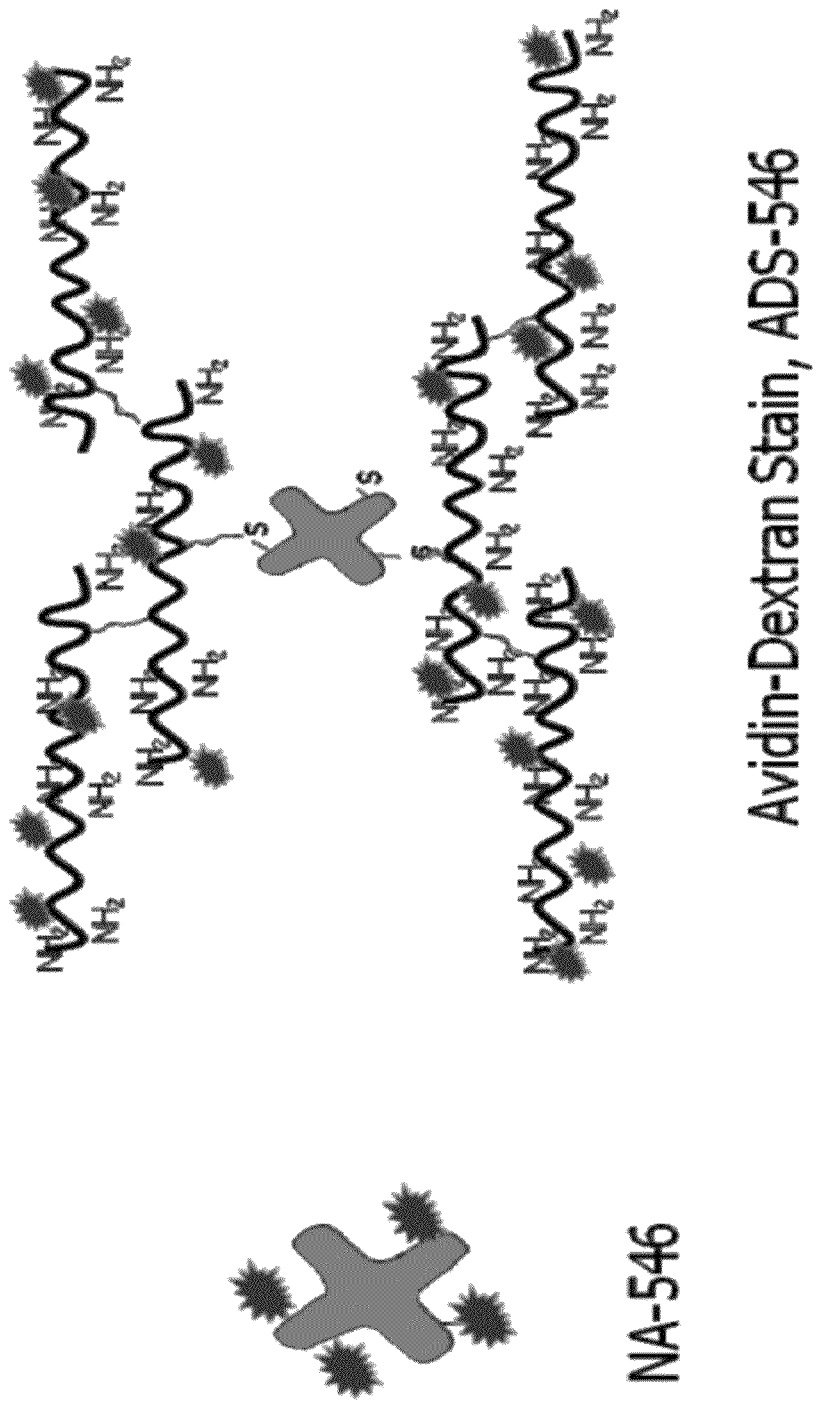
FIG. 5: Beyond NA: Amplified stains using dextran. A drawing representation of the avidin-dextran conjugate labeled with fluorescent dye (exemplary detectable reagent containing detectable entity). The number of theoretical dyes per avidin would be higher than avidin only labeling.

A drawing representation of the avidin dextran conjugate (avidin-based detectable reagent) labeled with fluorescent dye is shown in FIG. 5. The number of theoretical dyes per avidin would be higher than avidin only labeling.

Figure 6:
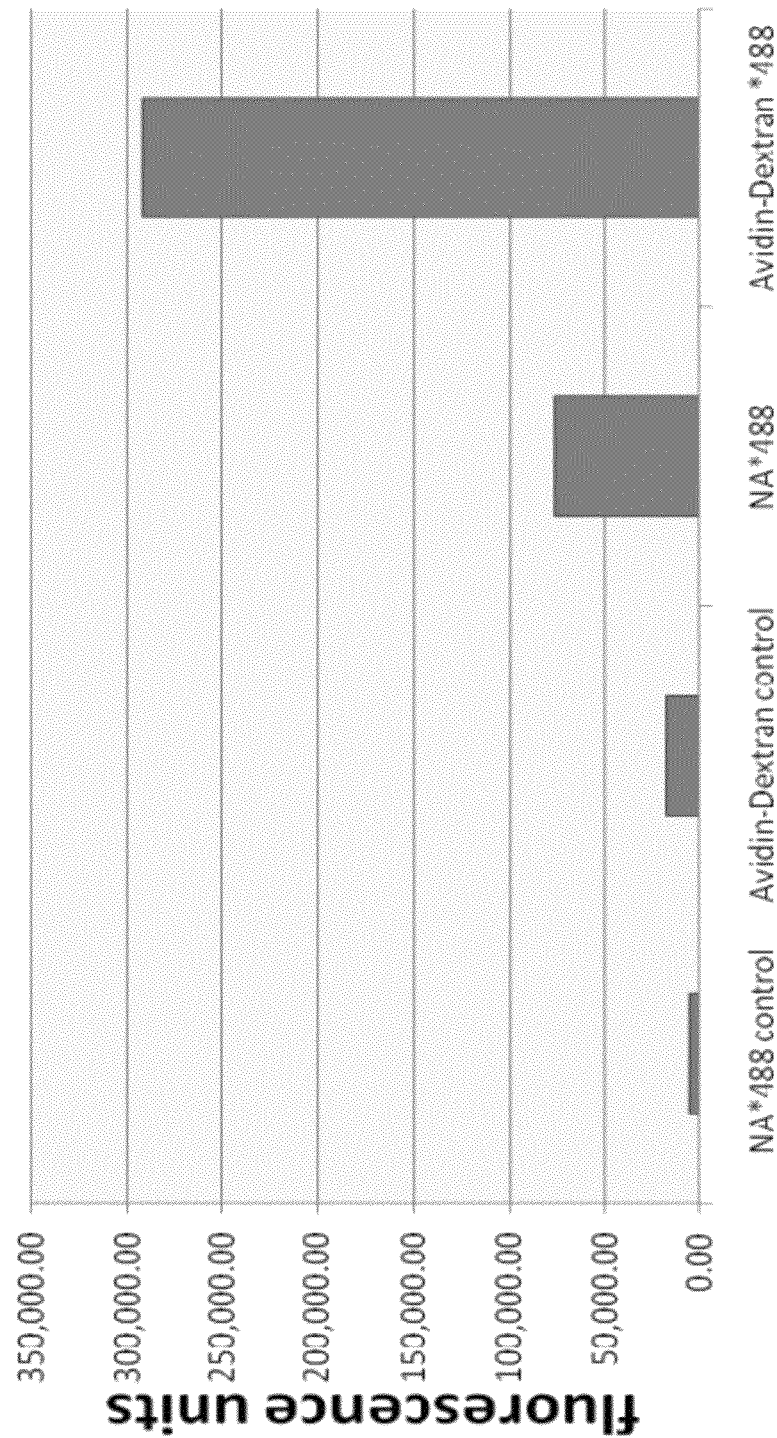
FIG. 6: FACS fluorescent intensity on SKOV cells. Shows FACS analysis of SKOV cells incubated with a single biotinylated EpCAM antibody which were subsequently incubated with avidin-488 (green fluorescently labeled) and avidin-dextran-488. The first and second bars are the staining intensity of control cells with avidin or conjugate added, but no biotinylated EpCAM antibody. The third bar shows the staining intensity of the cells when avidin-488 was added to EpCAM treated cells. The fourth bar shows the staining intensity of the same cells incubated with avidin-dextran-488. These data indicate that the avidin-dextran conjugate had 3-4 times more fluorescent intensity than avidin-488 alone.
Figure 7:
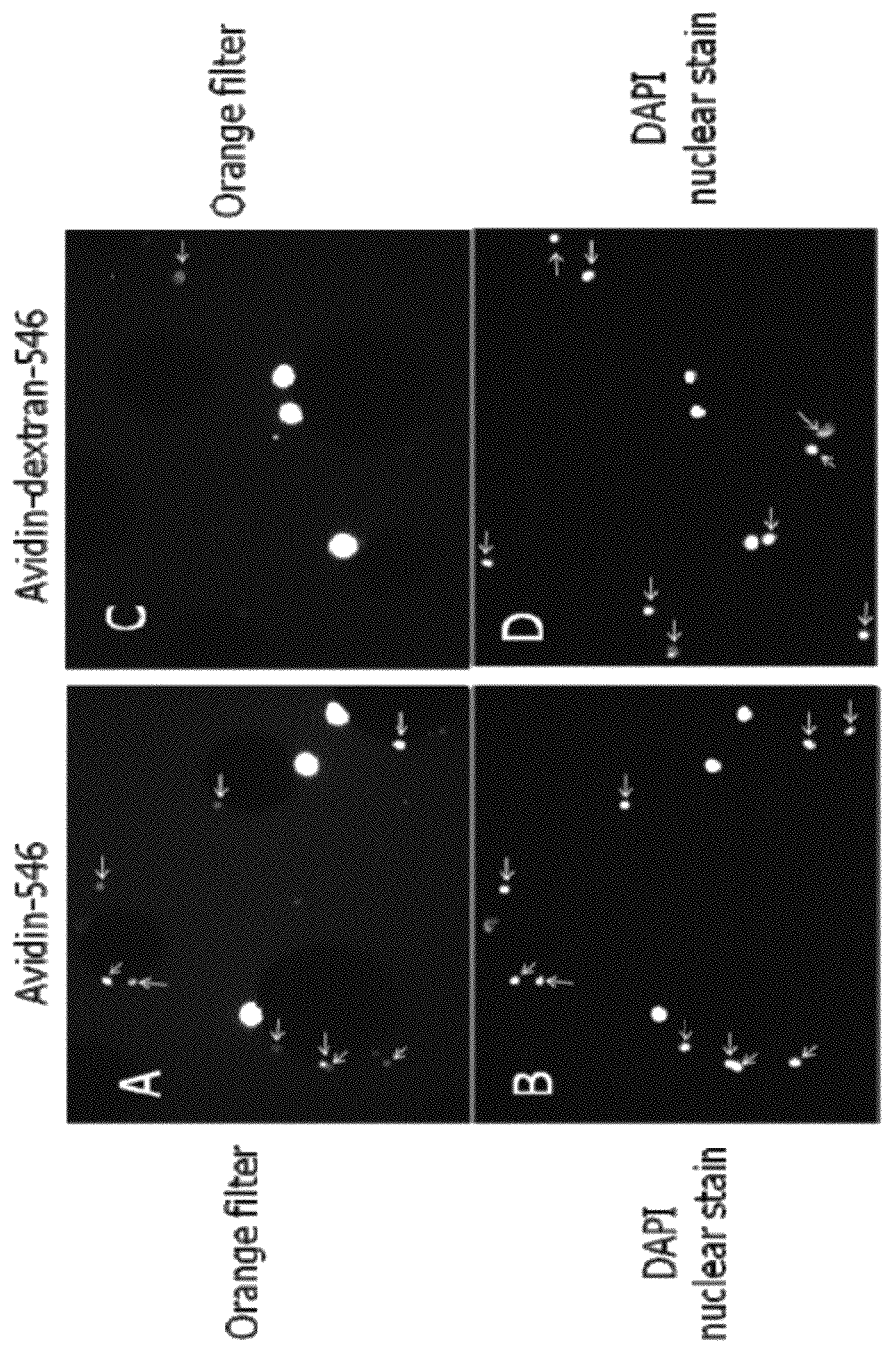
FIG. 7: ADS Advantage II—Lower WBC Staining Shows the relative staining of SKOV and white blood cells (WBC). In this experiment the SKOV cells were spiked into blood and then processed as usual and captured on the micro-channel using the antibody cocktail of capture antibodies. The cells in different channels were then stained only with avidin-546 (546 indicates an orange fluorescent dye) and avidin-dextran-546. In the A and C panels the large highly stained cells were orange fluorescently labeled. The matched B and D images from the microscope were the DAPI stained cells, which revealed nucleated cells whether they were SKOV or WBC. In the case of panel B there were 10 DAPI positive WBCs detected (indicated by the arrows). In the image-matched slide A where the orange fluorescently labeled cells were revealed using the appropriate filter, 9 out of 10 of the WBC could be visualized as containing various levels of orange stain after an exposure of 2 seconds. When the same criteria were applied to the avidin-dextran treated channels, 9 DAPI positive WBC were detected in panel D, while in the matched panel C using the orange filter only 1 of the WBC was faintly detectable after a 2 second exposure. This experiment demonstrated that the avidin-dextran stain not only stained cells more intensely than avidin alone (FIG. 6) but had less background staining on the surrounding WBC.
Figure 8:
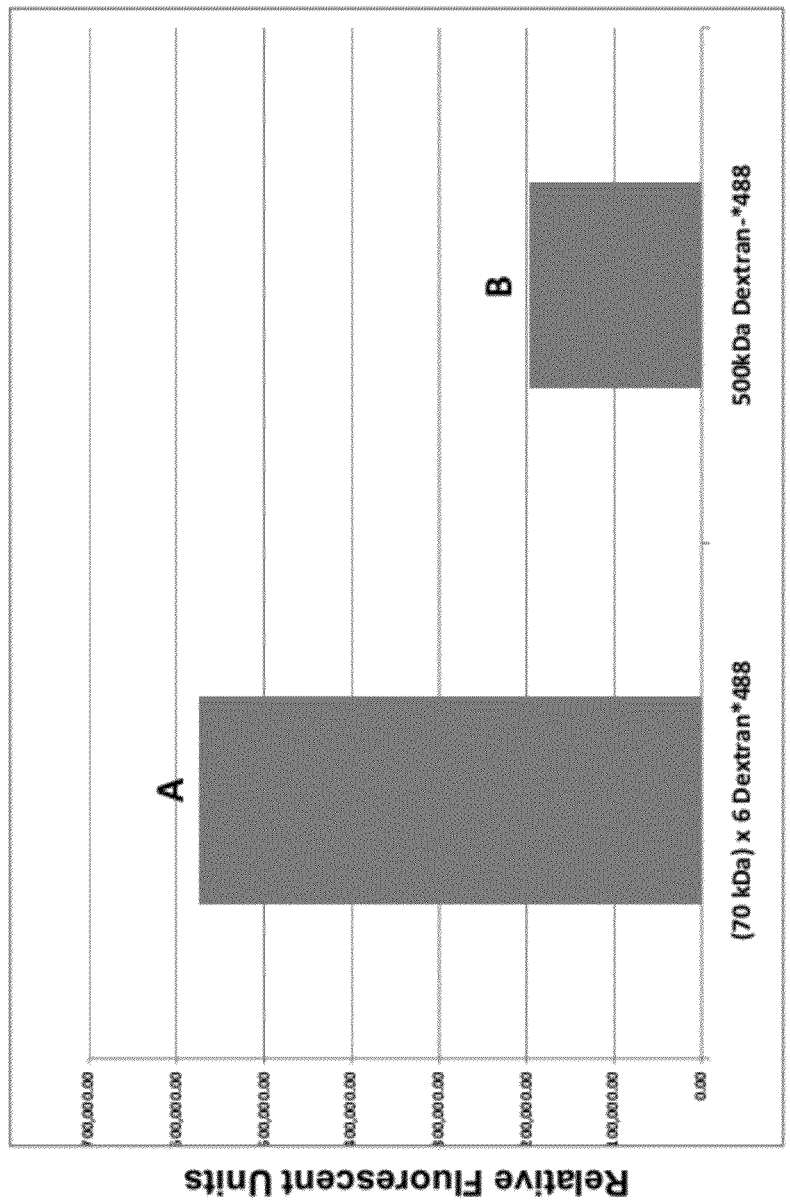
FIG. 8: Relative Fluorescence between 70 kDa×6 Dextran*488 and 500 kDa Dextran. A comparison of the relative fluorescence intensity obtained by labeling SKOV cells using the avidin-dextran conjugate of the current invention (A) compared to an avidin-dextran conjugate prepared in an identical manner except using a single 500 kDa molecule of dextran-amine conjugated to avidin and fluorescently labeled with AlexaFluor-488 (B). While each core avidin-dextran conjugate contained a comparable weight of dextran per molecule of avidin, and each was derivatized with the same molar excess of NHS-AlexaFluor-488, the sequentially prepared (inter-connected dextran) conjugate resulted in a nearly 3-fold higher level of fluorescent labeling of the cells.

FACS analysis of SKOV cells incubated with a single biotinylated EpCAM antibody which were subsequently incubated with avidin-488 (green fluorescently labeled avidin) and avidin-dextran-488 (avidin-based detectable reagent 70 kDa dextran) is shown in FIG. 6. The first and second bars are the staining intensity of control cells with avidin or conjugate added, but no biotinylated EpCAM antibody. The third bar shows the staining intensity of the cells when avidin-488 was added to EpCAM treated cells. The fourth bar shows the staining intensity of the same cells incubated with avidin-dextran-488. These data indicate that the avidin-dextran conjugate had 3-4 times more fluorescent intensity than avidin-488 alone.

The relative staining of SKOV and white blood cells (WBC) with avidin-546 (orange fluorescently labeled avidin) and avidin-dextran-546 (avidin-based detectable reagent 70 kDa dextran). In this experiment the SKOV cells were spiked into blood and then processed as usual and captured on the micro-channel using the antibody cocktail of capture antibodies. The cells in different channels were then stained only with avidin-546 (546 indicates an orange fluorescent dye) and avidin-dextran-546. In the A and C panels the large highly stained cells were orange fluorescently labeled. The matched B and D images from the microscope were the DAPI stained cells, which revealed nucleated cells whether they were SKOV or WBC. In the case of panel B there were 10 DAPI positive WBCs detected (indicated by the arrows). In the image-matched slide A where the orange fluorescently labeled cells were revealed using the appropriate filter, 9 out of 10 of the WBC could be visualized as containing various levels of orange stain after an exposure of 2 seconds. When the same criteria were applied to the avidin-dextran treated channels, 9 DAPI positive WBC were detected in panel D, while in the matched panel C using the orange filter only 1 of the WBC was faintly detectable after a 2 second exposure. This experiment demonstrated that the avidin-dextran stained not only stains cells more intensely than avidin alone (FIG. 6) but had less background staining on the surrounding WBC.

A comparison of the relative fluorescence intensity obtained by labeling SKOV cells using the avidin-dextran conjugate stain of the current invention (A; avidin-based detectable reagent 70 kDa dextran) compared to an avidin-dextran conjugate prepared in an identical manner except using a single 500 kDa molecule of dextran-amine conjugated to avidin and fluorescently labeled with AlexaFluor-488 (B; avidin-based detectable agent 500 kDa dextran). While each core avidin-dextran conjugate contained a comparable weight of dextran per molecule of avidin, and each was derivatized with the same molar excess of NHS-AlexaFluor-488, the sequentially prepared conjugate containing layered or branched dextran resulted in nearly 3-fold higher level of fluorescent labeling of the cells.

All publications discussed and cited herein are incorporated herein by reference in their entireties. It is understood that the disclosed invention is not limited to the particular methodology, protocols and materials described as these can vary. It is also understood that the terminology used herein is for the purposes of describing particular embodiments only and is not intended to limit the scope of the present invention which will be limited only by the appended claims.

Those skilled in the art will recognize, or be able to ascertain using no more than routine experimentation, many equivalents to the specific embodiments of the invention described herein. Such equivalents are intended to be encompassed by the appended claims.

The invention claimed is:

1. A detectable reagent comprising:
a binding moiety conjugated to a dextran component, wherein the dextran component has a total of about 4 to about 8 dextrans per binding moiety and the binding moiety is not a dextran or a target entity in a sample, and wherein a detectable entity is conjugated to the dextran component.

2. The detectable reagent of claim 1, wherein each dextran is from about 30 kDa to about 100 kDa molecular weight.

3. The detectable reagent of claim 1, wherein each dextran is about 70 kDa molecular weight.

4. The detectable reagent of claim 1, wherein each dextran has substantially the same molecular weight.

5. The detectable reagent of claim 1, wherein at least one dextran has a molecular weight different from another dextran.

6. The detectable reagent of claim 1, wherein the detectable entity is a fluorophore.

7. The detectable reagent of claim 6, wherein the fluorophore is selected from a fluorophore with green fluorescence, orange fluorescence, red fluorescence, and far red fluorescence.

8. The detectable reagent of claim 6, wherein the fluorophore is selected from a fluorophore with excitation and emission spectra in the range of about 350 nm to 775 nm.

9. The detectable reagent of claim 8, wherein the fluorophore is selected from a fluorophore with excitation and emission spectra of about 346 nm/446 nm, about 494 nm/519 nm, about 554 nm/570 nm, about 555 nm/572 nm, about 590 nm/617 nm, about 651 nm/672 nm, about 679 nm/702 nm and about 749 nm/775 nm.

10. The detectable reagent of claim 1, wherein the binding moiety is selected from the group consisting of avidin, streptavidin, biotin, digoxigenin, immunoreagent, oligonucleotide, peptide, protein, nucleic acid, peptide nucleic acid, protein A, protein G, a derivative thereof, and a ligand-binding portion thereof.

11. A method of making a detectable reagent comprising:
providing a dextran component comprising a plurality of inter-connected dextran;
conjugating the dextran component with a binding moiety to form a dextran-binding moiety complex, wherein the binding moiety is not a dextran or a target entity in a sample, and wherein the dextran-binding moiety complex has a total of about 4 to about 8 dextrans per binding moiety; and
attaching a detectable entity to the dextran-binding moiety complex.

12. A method of making a detectable reagent comprising:
conjugating a binding moiety to a dextran to form a core dextran-binding moiety, wherein the binding moiety is not a dextran or a target entity in a sample;
reacting the core dextran-binding moiety with one or more dextrans to form a dextran-binding moiety complex which contains a total of about 4 to about 8 dextrans per binding moiety; and
attaching a detectable entity to the dextran-binding moiety complex.

13. The method of claim 12, wherein the binding moiety is avidin or strepavidin.

14. A method for detecting or quantifying a target molecule comprising:
contacting the detectable reagent of claim 1 with a sample suspected of containing a target molecule, wherein the binding moiety is capable of binding to the target molecule; and
detecting a signal of the detectable entity thereby detecting or quantifying the target molecule.

15. The detectable reagent of claim 1, wherein the total molecular weight of dextrans is at least 500 kDa.

16. The detectable reagent of claim 1, wherein the dextrans within the dextran component are inter-connected and configured in a layered configuration or branched configuration.

17. The detectable reagent of claim 1, wherein each dextran is from 30 kDa to 100 kDa molecular weight.

18. The detectable reagent of claim 1, wherein each dextran is from about 50 kDa to about 70 kDa molecular weight.

19. The detectable reagent of claim 1, wherein the detectable reagent contains a total of about 6 dextrans per binding moiety.

20. The detectable reagent of claim 1, wherein the detectable reagent contains a total of 6 dextrans per binding moiety.

21. The detectable reagent of claim 1, wherein the detectable reagent provides an enhanced, increased or amplified detection when compared to a detection achieved from a binding moiety conjugated to a detectable entity in the absence of dextrans or a binding moiety conjugated to a single dextran containing a detectable entity.

22. The detectable reagent of claim 21, wherein the enhanced, increased or amplified detection is at least about 2 fold more signal compared to detection achieved from a binding moiety conjugated to a detectable entity in the absence of dextrans or a binding moiety conjugated to a single dextran containing a detectable entity.

23. A method of making a detectable reagent of claim 1 comprising:
derivatizing a dextran-amine to generate maleimide functional groups;
derivatizing a binding moiety to generate thiol functional groups, wherein the binding moiety is not a dextran or a target entity in a sample;
reacting the derivatized binding moiety with a molar ratio of one or more derivatized dextran-amine to form a dextran-binding moiety;
derivatizing the dextran-binding moiety to generate one or more thiol groups per dextran;
reacting the derivatized dextran-binding moiety with a molar ratio of one or more derivatized dextran-amine to form an inter-connected dextran-binding moiety complex, wherein the dextran-binding moiety complex has a total of about 4 to about 8 dextrans per binding moiety; and
reacting the inter-connected dextran-binding moiety complex with a molar ratio of one or more detectable entities to form a detectable reagent.

24. The detectable reagent of claim 1, wherein the binding moiety is avidin or streptavidin.

25. The detectable reagent of claim 1, wherein the detectable reagent has a total of 4 to 8 dextrans per binding moiety.

* * * * *